United States Patent [19]
Devanathan

[11] Patent Number: 5,387,243
[45] Date of Patent: Feb. 7, 1995

[54] METHOD FOR CONVERTING A CEMENTABLE IMPLANT TO A PRESS FIT IMPLANT

[75] Inventor: Thirumalai Devanathan, Warsaw, Ind.

[73] Assignee: Zimmer, Inc., Warsaw, Ind.

[21] Appl. No.: 975,757

[22] Filed: Nov. 23, 1992

[51] Int. Cl.⁶ .............................................. A61F 2/28
[52] U.S. Cl. ....................................... 623/23; 623/16
[58] Field of Search ................ 623/16, 17, 18, 20, 623/22, 23

[56] References Cited

U.S. PATENT DOCUMENTS

| | | | |
|---|---|---|---|
| 3,605,123 | 9/1971 | Hahn | 3/1 |
| 3,662,405 | 5/1972 | Bortz et al. | 3/1 |
| 3,720,996 | 3/1973 | Tschermak | 29/527.1 |
| 3,855,638 | 12/1974 | Pilliar | 3/1 |
| 3,893,196 | 7/1975 | Hochman | 3/1.91 |
| 3,905,777 | 9/1975 | Larcoix | 29/183.5 |
| 3,906,550 | 9/1975 | Rostoker et al. | 3/1.912 |
| 3,938,198 | 2/1976 | Kahn et al. | 3/1.912 |
| 4,007,494 | 2/1977 | Sauer | 3/1.9 |
| 4,058,581 | 11/1977 | Park | 264/136 |
| 4,064,567 | 12/1977 | Burstein et al. | 3/1.91 |
| 4,164,794 | 8/1979 | Spector et al. | 3/1.91 |
| 4,202,055 | 5/1980 | Reiner et al. | 3/1.91 |
| 4,205,400 | 6/1980 | Shen et al. | 3/1.91 |
| 4,213,816 | 7/1980 | Morris | 156/245 |
| 4,237,559 | 12/1980 | Borom | 3/1.9 |
| 4,351,069 | 9/1982 | Ballintyn et al. | 3/1.912 |
| 4,356,571 | 11/1982 | Esper et al. | 3/1 |
| 4,454,612 | 6/1984 | McDaniel et al. | 3/1.913 |
| 4,479,271 | 10/1984 | Bolesky et al. | 3/1.911 |
| 4,501,031 | 2/1985 | McDaniel et al. | 3/1.911 |
| 4,535,485 | 8/1985 | Ashman et al. | 623/16 |
| 4,536,894 | 8/1985 | Galante et al. | 623/22 |
| 4,550,448 | 11/1985 | Kenna | 623/16 |
| 4,589,883 | 5/1986 | Kenna | 623/22 |
| 4,636,218 | 1/1987 | Fukuura et al. | 623/18 |
| 4,636,219 | 1/1987 | Pratt et al. | 623/22 |
| 4,650,109 | 3/1987 | Crivella et al. | 228/194 |
| 4,650,489 | 3/1987 | Thompson | 623/16 |
| 4,662,887 | 5/1987 | Turner et al. | 623/16 |
| 4,673,409 | 6/1987 | Van Kampen | 623/23 |

FOREIGN PATENT DOCUMENTS

| | | |
|---|---|---|
| 0273871 | 7/1988 | European Pat. Off. ............. 623/23 |
| 89830101.5 | 3/1989 | European Pat. Off. . |
| 0366603 | 5/1990 | European Pat. Off. ............. 623/23 |
| 0420435A2 | 3/1991 | European Pat. Off. . |
| 0484082A1 | 6/1992 | European Pat. Off. . |
| 33806/77 | 8/1977 | Germany . |
| 3625520 | 9/1987 | Germany ............................. 623/23 |
| 2142830 | 1/1985 | United Kingdom ................. 623/20 |
| 2163960A | 3/1986 | United Kingdom . |
| 2198356A | 6/1988 | United Kingdom . |
| 2216425A | 10/1989 | United Kingdom . |
| WO85/04323 | 10/1985 | WIPO . |

(List continued on next page.)

OTHER PUBLICATIONS

S. F. Hulbert, et al., Potential of Ceramic Materials as Permanently Implantable Skeletal Prosthesis, J. Biomed. Mater. Res., vol. 4, pp. 433–456 (1970).

(List continued on next page.)

*Primary Examiner*—David Isabella
*Attorney, Agent, or Firm*—Todd A. Dawson

[57] ABSTRACT

The set of implants and method of this invention provide for the conversion of an implant 10 intended for cemented fixation to a bone to an implant 10' intended for non-cemented fixation to a bone. The set of implants include a plurality of pads 20 each having a porous surface layer 24 bonded to a plate 22. A thin layer 30 of thermoplastic polymer is bonded to the opposite side of the plate 22. The implant 10 is provided with a generally smooth outer surface and is intended for cemented use for fixation to the bone. However, if during surgery, the surgeon determines that the patient may be better suited for a non-cemented implant, the modular porous pads 20 may be bonded to the implant 10 to form an implant 10' intended for non-cemented fixation to the bone.

3 Claims, 3 Drawing Sheets

U.S. PATENT DOCUMENTS

| | | | |
|---|---|---|---|
| 4,714,467 | 12/1987 | Lechner et al. | 623/16 |
| 4,718,912 | 1/1988 | Crowninshield | 623/23 |
| 4,722,870 | 2/1988 | White | 428/621 |
| 4,750,905 | 6/1988 | Koeneman et al. | 623/16 |
| 4,773,406 | 9/1988 | Spector et al. | 128/92 |
| 4,778,469 | 10/1988 | Lin et al. | 623/16 |
| 4,778,474 | 10/1988 | Homsy | 623/22 |
| 4,782,183 | 11/1988 | Casey et al. | 128/92 |
| 4,813,960 | 3/1989 | Muller | 623/22 |
| 4,865,607 | 9/1989 | Witzel et al. | 623/20 |
| 4,889,685 | 12/1989 | Shimamune et al. | 419/9 |
| 4,892,551 | 1/1990 | Haber | 623/23 |
| 4,902,297 | 2/1990 | Devanathan | 623/16 |
| 4,905,680 | 3/1990 | Tunc | 606/69 |
| 4,932,974 | 6/1990 | Pappas et al. | 623/16 |
| 4,938,772 | 7/1990 | Frey et al. | 623/23 |
| 4,938,774 | 7/1990 | Tepic | 623/23 |
| 4,955,911 | 9/1990 | Frey et al. | 623/16 |
| 4,976,738 | 12/1990 | Frey et al. | 623/16 |
| 4,978,355 | 12/1990 | Frey et al. | 623/16 |
| 4,978,358 | 12/1990 | Bobyn | 623/23 |
| 4,978,360 | 12/1990 | Devanathan | 623/66 |
| 4,997,444 | 3/1991 | Farling | 623/16 |
| 4,997,445 | 3/1991 | Hodorek | 623/16 |
| 5,002,580 | 3/1991 | Noble et al. | 623/23 |
| 5,013,315 | 5/1991 | Barrows | 606/71 |
| 5,013,324 | 5/1991 | Zolman et al. | 623/23 |
| 5,019,108 | 5/1991 | Bertin et al. | 623/23 |
| 5,037,442 | 8/1991 | Wintermantel et al. | 623/23 |
| 5,163,960 | 11/1992 | Bonutti | 623/16 |

OTHER PUBLICATIONS

S. F. Corcoran, J. M. Koroluk, J. r. Parsons, H. Alexander, and A. B. Weiss; The Development of a Variable Stiffness, Absorbable Composite Bone Plate pp. 136–145.

BASF Plastics, ULTRAPEK, High–heat-resistant polyaryletherketones (Peak) (Product Line Properties Processing) pp. 1–43.

Murali Jasty, M. D., et al.Bone Ingrowth Into a Low Modulus Composite Plastic Porous–Coated Canine Femoral Component, Oct. 29, 1990 pp. 1–18.

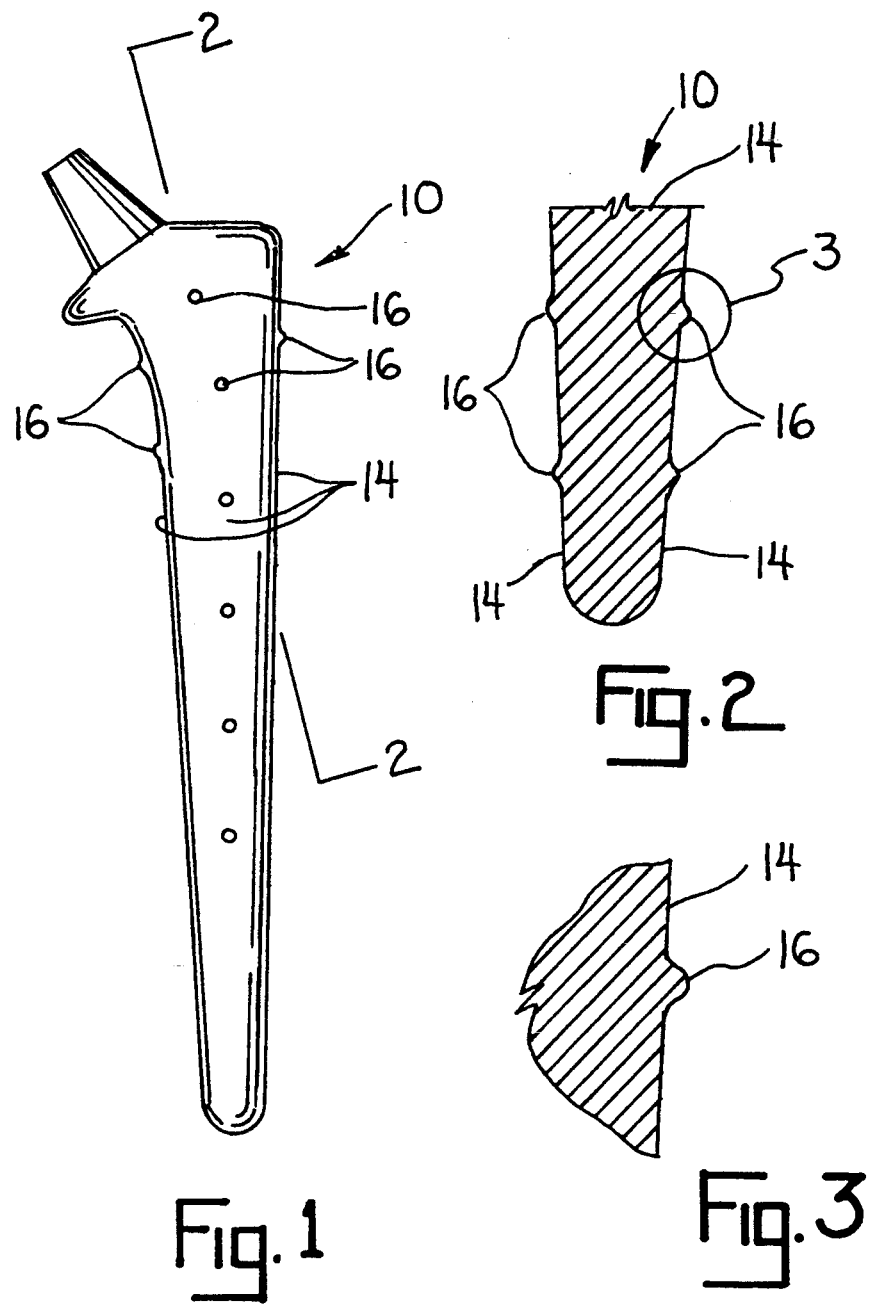

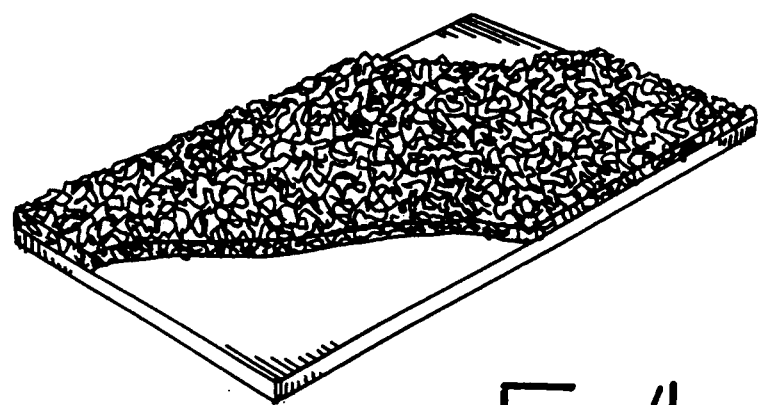
Fig. 4
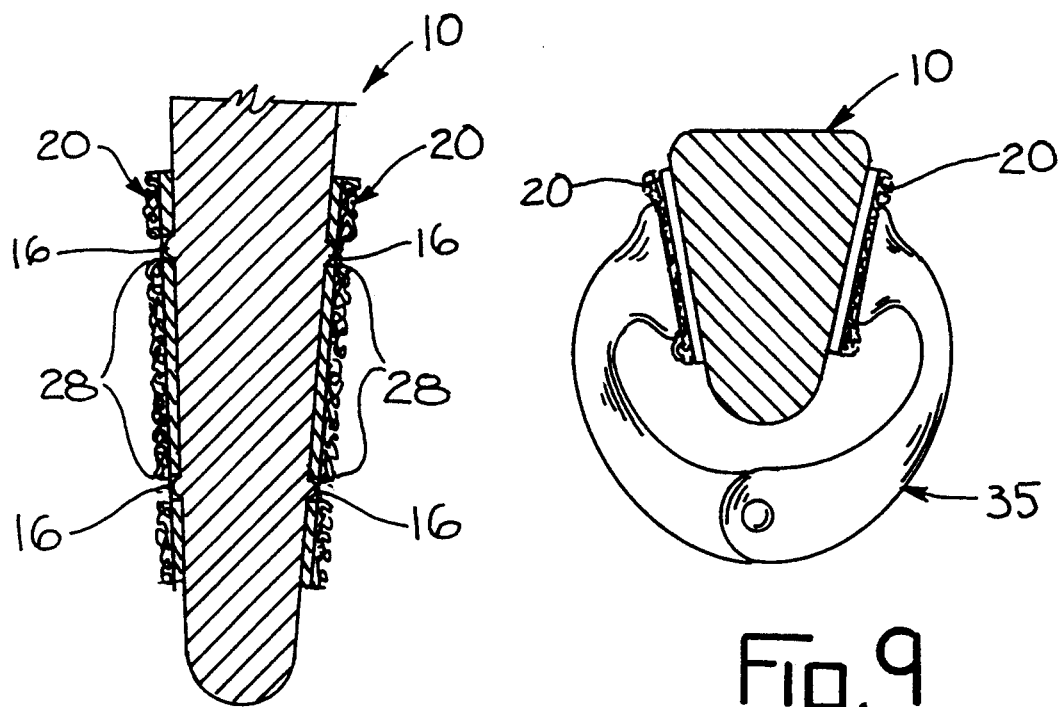
Fig. 8
Fig. 9

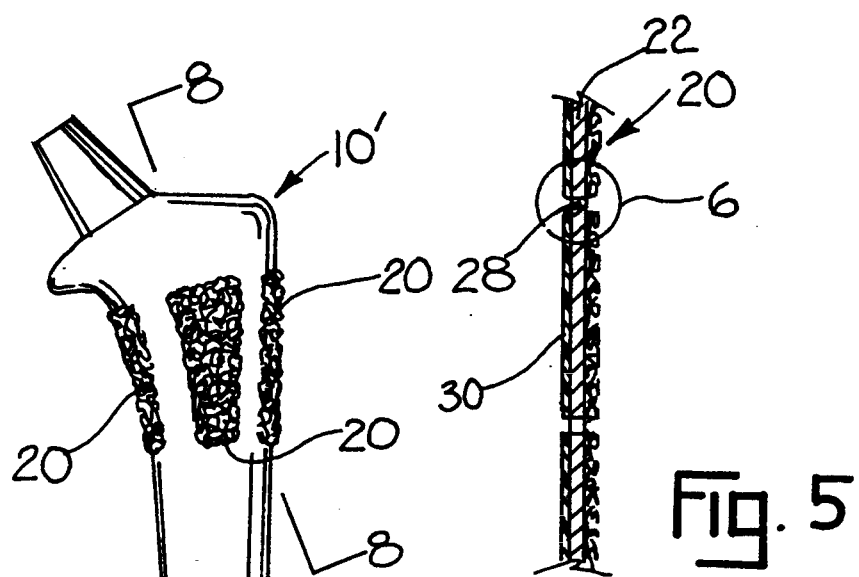
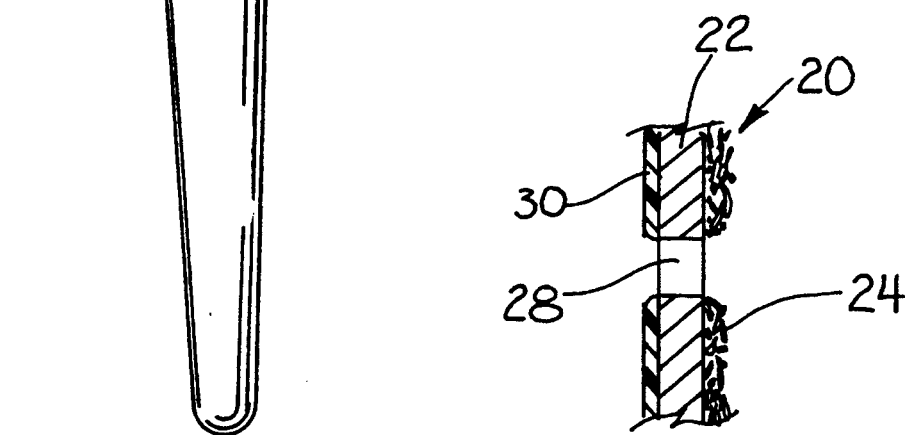

METHOD FOR CONVERTING A CEMENTABLE IMPLANT TO A PRESS FIT IMPLANT

Field of the Invention

This invention relates to orthopedic implants intended for cemented use within the intramedullary canal of a patient, more particularly, the invention relates to a set of modular prosthetic implants for converting an implant intended for cemented use into an implant applicable to a non-cemented use.

BACKGROUND OF THE INVENTION

In general, orthopaedic implants can be broken down into two rather broad classifications, i.e. cemented and non-cemented. A cemented implant is one that is specifically designed to be held in contact with a bone by a layer of cement. U.S. Pat. No. 3,228,393 illustrates an implant intended for cemented use. A non-cemented implant, as defined here, is one that is specifically designed to have an initial fixation such as a press fit and a long term fixation such as bone growth into a portion of the implant. U.S. Pat. No. 3,906,550 illustrates an implant intended for non-cemented use. A non-cemented implant or press-fit implant is generally provided with some type of porous outer coating to promote bone growth about the implant and bone interdigitation within the porous structure. Two well-known porous surfaces for use as a porous surface are a wire mesh pad or a layer(s) of metal beads.

The choice between using a cemented or non-cemented implant is a decision left to the orthopaedic surgeon. In general there are several factors affecting the decision such as patient age, patient activity, and the quality of the bone stock as determined by X-rays. These factors are presented here merely as an example; in practice, many other factors may play into the surgeon's choice between a cemented of non-cemented application.

Many of the factors affecting the decision may be based primarily on X-rays or other radiographic imaging data, each of which have inherent limitations. Therefore, until the surgeon actually exposes the bone which will accept the implant, a degree of uncertainty may exist.

It is conceivable that a surgeon who originally decided on a cemented implant may, after exposing the bone, determine that a non-cemented implant would be better for the patient. The problem is that with the prior art implants, if the alternative non-cemented implant is not available, the surgeon may have no choice but to continue with the procedure and implant a less than optimal implant. To compensate for this eventuality, a surgeon could request the hospital to have in inventory and on hand during surgery both types of implants.

SUMMARY OF THE INVENTION

The set of implants and method of this invention provides a solution to those discussed above by providing a plurality of pads each having a porous surface layer metallurgically bonded to a plate. A thin layer of thermoplastic polymer is bonded to the opposite side of the plate. The body of the implant is provided with a generally smooth outer surface and is intended for cemented use for fixation to the bone. However, if during surgery the surgeon determines that the patient may be better suited for a non-cemented implant, the modular porous pads may be bonded to the implant body. The modular porous pads are initially placed in contact with the body and properly aligned. The assembly of modular porous pads and implant body is then heated to a temperature of 780 degrees Fahrenheit (415 degrees Celsius). At this temperature, the thermoplastic polymer becomes molten and exhibits extremely good adhesive characteristics. The assembly is allowed to cool with the modular porous pads melt bonded to the implant body. At this point, the implant has been converted from an implant intended for cemented use to an implant intended for a non-cemented use.

In the preferred embodiment, the thermoplastic polymer of choice is from the polyaryletherketone family (PAEK). Specifically, a PAEK sold by BASF under the trade name Ultrapek® A3000. The PAEK polymers have been shown through experimentation to exhibit strong adhesive bonds with molybdenum alloy (Co—Cr—Mo) and titanium-vanadium-aluminum alloy (Ti-6A1-4V) commonly used for implant materials.

Accordingly, it is an advantage of the invention to provide for a novel set of orthopaedic implants which can be transformed from an implant intended for cemented use to an implant intended for a non-cemented use, implementing modular porous pads and a thin film of thermoplastic polymer to bond the pads to the implant body.

Another advantage of the invention is to provide for method of converting an orthopaedic implant intended for cemented use to an orthopaedic implant intended for a non-cemented use having at least one modular porous pad connected to the implant body by a thin film of thermoplastic polymer.

Another advantage of the invention is to provide for method of converting an orthopaedic implant intended for cemented use to an orthopaedic implant intended for a non-cemented use having at least one modular porous pad connected to the implant body by a thin film of thermoplastic polymer from the polyaryletherketone family (PAEK).

Another advantage of the invention is to provide a modular porous pad having a porous surface on one side and a thin film of thermoplastic polymer on the other side.

Other advantages of the invention will become apparent upon a reading of the following description taken with the accompanying drawings.

BRIEF DESCRIPTION OF THE DRAWINGS

FIG. 1 is an elevational view of an orthopaedic implant intended for cemented use within an intramedullary canal.

FIG. 2 is a sectional view taken along line 2—2 of FIG. 1.

FIG. 3 is an enlarged view of the area circled in FIG. 2 and identified by numeral 3.

FIG. 4 is a perspective view of a sheet of fiber metal bonded to a metal backing plate.

FIG. 5 is a cross section of a porous pad of the invention.

FIG. 6 is an enlarged view of the area circled in FIG. 5 and identified by numeral 6.

FIG. 7 is an elevational view of the implant of the invention intended for non-cemented fixation within an intramedullary canal.

FIG. 8 is a cross section taken from line 8—8 of FIG. 7.

FIG. 9 is a cross section of the implant of FIG. 7 and further illustrating a clamp attached thereto.

DESCRIPTION OF THE PREFERRED EMBODIMENT

The preferred embodiment herein described is not intended to be exhaustive or to limit the invention to the precise form disclosed. Rather, it is chosen and described to best explain the invention so that others skilled in the art might utilize its teachings.

FIG. 1 illustrates an orthopaedic implant 10 in the form of a hip stem implant. It should be understood that while the specification discloses the invention in conjunction with a hip stem implant, the invention has equal application to a wide variety of implants. As illustrated, implant 10 includes generally smooth outer surfaces. Since the outer walls of the implant, which will contact the bone, are smooth, the implant 10 of FIG. 1 is considered an implant intended for cemented use. In other words, the prepared intramedullary canal of the bone is filled with cement first and then the implant is inserted into the cement filled cavity. This process for implanting a cemented orthopaedic implant is well-known.

As illustrated in the figures, projections 16 extend outwardly a small distance from the outer walls 14 of the implant. In practice, these projections are spaced approximately 2 centimeters apart about the portion of the implant adapted to accommodate pads as explained below. In the embodiment of FIG. 1, hip stem 10 is suited for cemented implantation within a prepared intramedullary canal of a patient.

The set of implants of the invention further includes a plurality porous pads 20. Pad 20 may be formed in a variety of shapes to fit on the implant at different locations along its outer walls (see FIG. 7). Porous pad 20 includes a metal backing plate 22 and a porous outer layer 24 metallurgically bonded by a known process such as diffusion bonding or sintering. A thin film 30 of thermoplastic polymer is placed on each pad 20 on a side opposite porous layer 24.

To form porous pad 20, a sheet 23 of porous layer 24 is placed on top of a sheet 21 metal backing plate 22 and the porous sheet is metallurgically bonded to the plate by a known process (see FIG. 4). Next individual porous pads 20 (only one shown) are laser cut from the sheet. Again, it should be understood that the porous pads may be cut into any desired shape for placement on the implant. In the preferred embodiment, holes 28 are formed through the metal backing plate 22 and porous layer 24 (see FIGS. 5 and 6). Finally, a thin film 30 of the thermoplastic polymer is placed on metal backing plate 22 on the side opposite the porous layer 24.

The implant 10 of Fig. 1 which is intended for cemented fixation within the intramedullary cavity is transformed into the implant 10' of FIG. 7 which is intended for non-cemented fixation within the body in the following manner.

First, the surgeon, after deciding that the non-cemented or press fit version of the implant better suits the needs of the patient, selects the particular size and shape of porous pad 20 from a plurality of such pads (only one shown) provided in kit form and in sterile condition to the surgeon. A porous pad 20 is aligned on the implant such that a protrusion 16 extends into each hole 28. This provides the proper alignment between the porous pad 20 and the implant. To hold the assembly together, a spring clamp 35 is placed onto the assembly of pads and implant to place a slight clamping force against the pads 20 (see FIG. 9). Next, the assembly of implant 10 and porous pad 20 with clamp 35 are heated either in a convection oven or preferably by a conduction heater to heat the thin film 30 of thermoplastic polymer to a temperature around 780 degrees Fahrenheit (415 degrees Celsius). When the thin film 30 of thermoplastic layer is molten, it exhibits strong adhesive qualities and forms a melt bond with the metal plate 22 and the implant body 10. Once heated, the implant is allowed to cool and the clamp 35 is removed. The porous pads are now securely bonded to the implant and the implant with pads attached is ready for non-cemented insertion within the intramedullary canal of the patient.

It should be understood that the invention is not limited to use with hip stem implants but has wide applicability to a variety of implants which have cemented and non-cemented versions. It should also be understood that the porous layer may be formed from fiber metal as illustrated or from small metal beads. The invention would work equally as well with either choice.

Finally, it should be understood that the invention is not to be limited to the precise forms disclosed but may be modified within the scope of the appended claims.

I claim:

1. A method of converting an implant intended for cemented fixation to a bone to an implant intended for non-cemented fixation to a bone, said method comprising the steps of:
   a) providing an orthopaedic implant having generally smooth outer walls, said implant being configured for insertion within a cement filled intramedullary canal;
   b) providing a porous pad, said pad having a solid metal layer with a porous layer bonded to one side of the metal layer, a second side of the metal layer carrying a thin film of thermoplastic polymer;
   c) placing said porous pad in contact with one of the generally smooth walls of said orthopaedic implant configured for insertion within a cement filled intramedullary canal such that said thin film of thermoplastic polymer is between the metal plate and the wall of the implant;
   d) heating said implant and said porous pad to cause said thin film of thermoplastic polymer to become molten, wherein said thermoplastic polymers exhibit adhesive characteristics when molten to bond said porous plate to said implant; and
   e) cooling said implant with porous pads bonded thereto, wherein said implant with porous pad attached is configured for a press fit insertion within a non-cement filled intramedullary cavity.

2. The method of claim 1 further including the steps of:
   a) providing at least one protrusion extending outwardly from the generally smooth walls of the implant;
   b) providing at least one bore extending through said metal layer of said porous pad;
   c) aligning said porous pad with said implant such that said protrusion extends into said bore.

3. The method of claim 1 wherein step c) includes the step of:
   a) providing a clamp to temporarily secure the porous pad to the implant prior to heating.

* * * * *